United States Patent [19]
Nichols

[11] 4,347,946
[45] Sep. 7, 1982

[54] SUCTION SYSTEM WITH COVER-PORT CAP ATTACHMENT BREAKAWAY TAB

[76] Inventor: Robert L. Nichols, 808 Fort Worth St., Jacksonville, Tex. 75766

[21] Appl. No.: 264,611

[22] Filed: May 18, 1981

Related U.S. Application Data

[63] Continuation of Ser. No. 955,531, Oct. 30, 1978, abandoned.

[51] Int. Cl.³ .................... A61M 1/00; B65D 55/16; B65D 41/18; B65D 47/14
[52] U.S. Cl. .................. 220/375; 128/276; 150/0.5; 222/541; 222/543; 215/309
[58] Field of Search .............. 220/306, 339, 375; 215/306, 309; 222/541, 543; 150/0.5; 128/276, 277, 278

[56] References Cited
U.S. PATENT DOCUMENTS

| | | | |
|---|---|---|---|
| 3,013,308 | 12/1961 | Armour | 220/339 |
| 3,031,111 | 4/1962 | Stull | 222/543 |
| 3,195,784 | 7/1965 | Aaland | 222/543 |
| 3,685,517 | 8/1970 | Reynolds | |
| 3,843,016 | 10/1974 | Bornhorst | 215/309 |
| 3,965,902 | 6/1976 | Reilly | |

FOREIGN PATENT DOCUMENTS 1372428  8/1964  France .................... 215/306

Primary Examiner—George E. Lowrance
Attorney, Agent, or Firm—Richards, Harris & Medlock

[57] ABSTRACT

An attachment breakaway tab (60) is provided for use in a suction system (10) for draining fluid from a source. The suction system (10) includes a fluid receptacle (12) and a cover member (14). The cover member (14) includes ports (16, 18, 20). Cap members (30, 40, and 50) are provided to engage and close the ports (16, 18, 20). The cap members (30, 40, 50) are permanently attached to the cover member (14) using restraining lines (32, 42, 52). A breakaway tab (60) temporarily attaches cap members (30, 40, 50) to the cover member (14) of the fluid receptacle (12) and is severable to permit cap members (30, 40, 50) to be disengaged from the edge of the cover member (14) to permit cap members (30, 40, 50) to be moved to engage the ports (16, 18, 20), while being attached to the cover member (14) using restraining lines (32, 42, 52).

1 Claim, 6 Drawing Figures

SUCTION SYSTEM WITH COVER-PORT CAP ATTACHMENT BREAKAWAY TAB

This is a continuation of application Ser. No. 955,531, filed Oct. 30, 1978, now abandoned.

TECHNICAL FIELD

This invention relates to medical suction receptacle assemblies for draining fluid from a patient, and more particularly to a cover-port cap attachment breakaway tab.

BACKGROUND ART

During the course of a surgical operation on a patient, it is often necessary to remove from the site of the operation various body fluids including blood, clots and other viscid fluids which tend to collect at the operation site. Removal of such body fluids is generally accomplished using an aspirator connected to a source of vacuum to draw the fluids through a suitable tube for deposit into a collection receptacle.

Body fluid storage and collection receptacles for use in such systems are well known in the art. Typically, such receptacle assemblies include a receptacle and a cover which are secured together with a leak tight seal. Two connections are provided in the cover, including a vacuum port for being connected by a tube or other suitable connection to a source of vacuum, for example, a vacuum pump or hospital vacuum outlet station. The other connection comprises a fluid receiving port which is connected through a drainage tube to the surgical operating site on a patient.

In such suction receptacle assemblies, the ports contained within the cover are often closed by caps to prevent contaminants from entering the receptacle prior to the receptacle's interconnection to the vacuum source and drainage tube. Such port caps are also used to close the ports after the receptacle has been filled with fluids to permit transportation of the filled receptacle for discarding or emptying. Additionally, a pour spout port may be provided in the cover, also requiring a cap for closure.

Heretofore such caps have been attached to the receptacle cover using a single flexible plastic restraining line. However, this attachment technique permits the port caps to hang or dangle from the receptacle cover and thus to enter the interior of the receptacle when the cover is being affixed to the receptacle. In the course of assemblying the cover to the receptacle, the port covers catch between the receptacle cover and the receptacle to interfere and prevent the formation of a fluid tight seal between the receptacle cover and receptacle. Further, the closing of the receptacle cover and receptacle sometimes serrates the restraining line and port covers are thereby severed from the receptacle cover and lost. Therefore, the ports cannot be closed to maintain the fluid within the receptacle.

Prior art port cap attachment systems are difficult to manufacture in that the port cap and restraining line are typically molded from plastic together with the receptacle cover in a continuous flow stream. This results in the port cap mold not receiving sufficient plastic material resulting in inadequate plastic injection, termed "short shots", resulting in defective caps. As there is only one point of entry for the plastic material to enter the cap mold cavity, it is difficult to supply enough plastic material to completely fill the mold cavity to mold the cap.

A need has thus arisen for a receptacle cover-port cap attachment system for use in a suction receptacle for preventing port caps from interfering with the seal between the receptacle cover and receptacle and the inadvertent serration of the restraining line from the receptacle cover. A need has further arisen for a port cap attachment system to enable uniform molding of the receptacle cover, restraining line and port cap to avoid short shots in the molding process.

DISCLOSURE OF THE INVENTION

In accordance with the present invention, a receptacle cover-port cap attachment breakaway tab is provided for use with a suction receptacle assembly for attaching port caps to receptacle covers.

In accordance with the present invention, in a suction system for draining fluid from a source, the system including a receptacle cover having at least one port, a port cap is provided and includes a port closure member. A flexible connecting line is integrally attached at one end to the port closure member and at a second end to the receptacle cover at a first point of attachment for permanently attaching the port closure member to the edge of the receptacle cover. The flexible connecting line has a sufficient length to allow the port closure member to be attached to a port. A breakaway tab is provided for temporarily attaching the port closure member to the edge of the receptacle cover at a second point of attachment spaced apart from the first point of attachment, such that the breakaway tab is severable for allowing the port closure member to be disengaged from the edge of the receptacle cover at the second point of attachment to permit the port closure member to be moved to engage and close a port.

BRIEF DESCRIPTION OF DRAWINGS

For a more complete understanding of the present invention and for further objects and advantages thereof, reference is now made to the following Detailed Description taken in conjunction with the accompanying drawings, in which.

DETAILED DESCRIPTION

Figure 1:
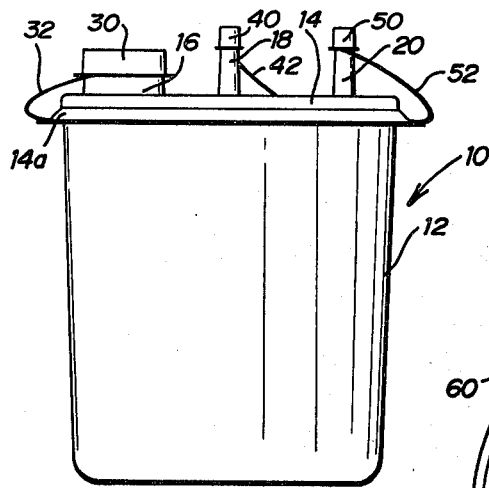
FIG. 1 is a side elevational view illustrating a suction receptacle utilizing the attachment breakaway tab assembly of the present invention.

FIG. 1 illustrates a suction receptacle assembly generally identified by the numeral 10 utilizing the present invention. Suction receptacle assembly 10 includes a suction receptacle 12, which may be formed of impact resistant, clear polystyrene plastic material to provide an implosion proof receptacle. Suction receptacle 12 is provided with a cover member 14 which is secured in a fluid tight relationship to suction receptacle 12 as is well known in the art. Cover member 14 includes a pour spout port 16 for ease in emptying collected fluid contained within suction receptacle 12. A source of vacuum, for example, a vacuum pump or hospital vacuum outlet station, is applied through a vacuum port 18 integrally formed with cover member 14. Cover member 14 further includes a fluid inlet port 20 for receiving a tube (not shown) which extends to a patient from which drainage is to be effected.

Figure 3:
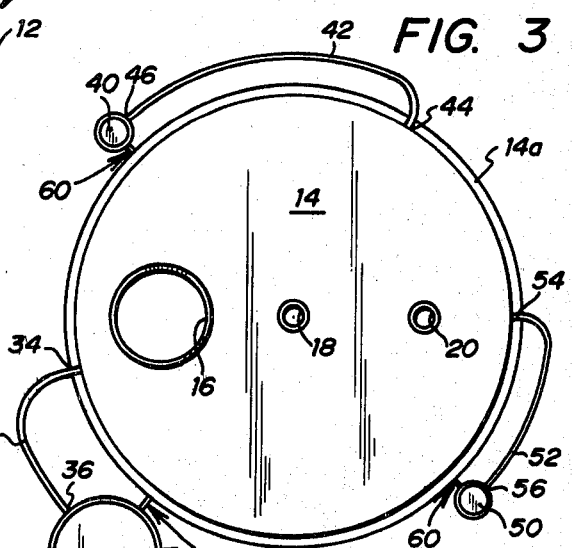
FIG. 3 is a top plan view of the suction receptacle illustrated in FIG. 2 showing the connection of the port caps to the receptacle cover prior to being severed from the receptacle cover.
Figure 2:
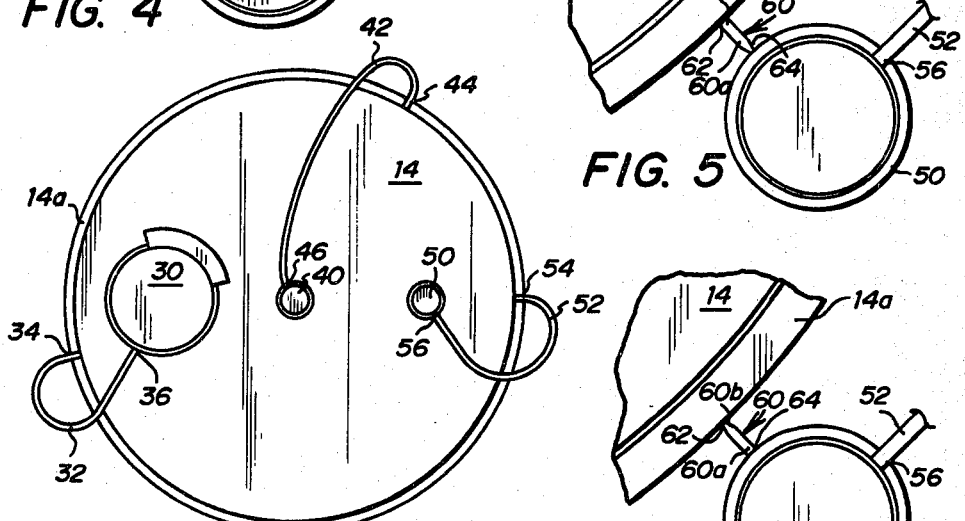
FIG. 2 is a top plan view of the suction receptacle illustrated in FIG. 1.

Referring simultaneously to FIGS. 1, 2, and 3, pour spout port 16 is provided with a cap member 30 adapted to engage and close pour spout port 16. Cap member 30 is permanently affixed to edge 14a of cover member 14 using a restraining line 32. In the preferred embodiment, restraining line 32 has a length of approximately two inches. Restraining line 32 is a flexible plastic elongate member and is integrally molded to cover member 14 and cap member 30. Restraining line 32 extends between a point of attachment 34 at edge 14a of cover member 14 and a point of attachment 36 to cap member 30. Vacuum port 18 is similarly provided with a cap member 40 which is secured to cover member 14 using a restraining line 42. In the preferred embodiment, restraining line 42 has a length of approximately four inches. Restraining line 42 is integrally molded to cover member 14 and cap member 40 and extends between a point of attachment 44 to edge 14a of cover member 14 and to a point of attachment 46 to cap member 40. Patient port 20 is provided with a cap member 50 that is integrally connected to cover member 14 using a restraining line 52. In the preferred embodiment, restraining line 52 has a length of approximately two inches. Restraining line 42 extends between a point of attachment 54 at edge 14a of cover member 14 to a point of attachment 56 to cap member 50. Cover member 14; cap members 30, 40 and 50; and restraining lines 32, 42 and 52 may be formed of, for example, polystyrene such as low density polystyrene or high impact styrene plastic material. It therefore can be seen that restraining lines 32, 42 and 52 permanently attach cap members 30, 40 and 50 to edge 14a of cover member 14.

Figure 4:
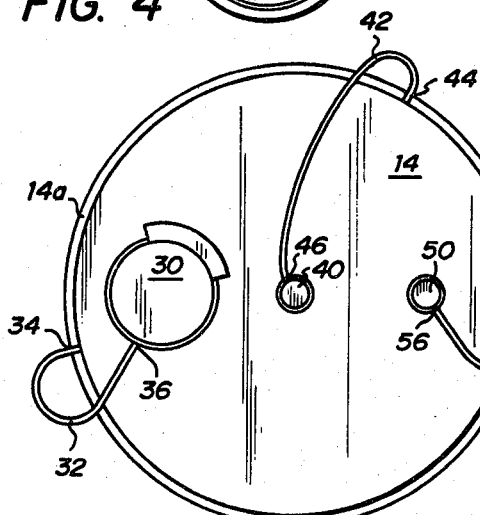
FIG. 4 is an enlarged top plan view of the breakaway tab assembly of the present invention.

Referring simultaneously to FIGS. 3 and 4, wherein like numerals are utilized for like and corresponding elements, the attachment breakaway tab of the present invention is illustrated and is generally identified by the numeral 60. FIGS. 3 and 4 illustrate breakaway tab 60 shown in the unsevered, engaged position for affixing cap members 30, 40 and 50 to edge 14a of cover member 14. In the preferred embodiment, breakaway tab 60 has a length of approximately ⅛ inch.

FIG. 4 illustrates an enlarged view of cap member 50 for purposes of illustration, it being understood that each cap member 30, 40 and 50 is similarly attached to cover member 14 using the breakaway tab 60 of the present invention. Breakaway tab 60 is integrally molded to cover member 14 and cap member 50 and extends from end 60b at a point of attachment 62 at edge 14a of cover member 14 to a point of attachment 64 to cap member 50 at end 60a of breakaway tab 60. Therefore it can be seen that breakaway tab 60 provides a second flow path of plastic material to cap member 50, such that plastic material in the molding process flows to cap member 50 through breakaway tab 60 and restraining line 52 to fully fill the mold to form cap member 50.

Figure 5:
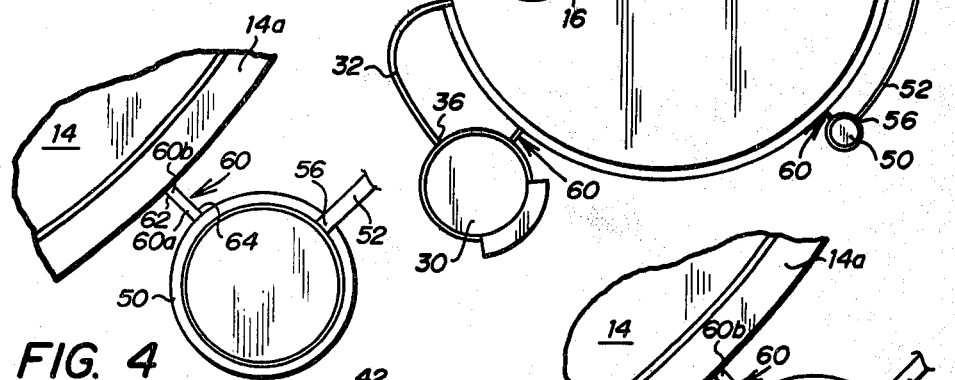
FIGS. 5 and 6 are enlarged top plan views showing additional attachment breakaway tab assemblies.
Figure 6:
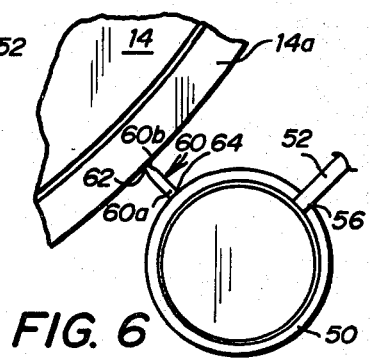

FIGS. 5 and 6 illustrate additional configurations of breakaway tab 60. FIG. 5 illustrates breakaway tab 60 having a reduced thickness or cross-sectional area at end 60a at point of attachment 64 between breakaway tab 60 and cap member 50 than at point of attachment 62 between breakaway tab 60 and cover member 14 at end 60b. In this configuration, when cap member 50 disengages cover member 14 to engage and close patient port 20 as illustrated in FIGS. 1 and 2, breakaway tab 60 severs from cap member 50 and remains integrally attached to cover member 14 at point of attachment 62. FIG. 6 illustrates breakaway tab 60 having a reduced thickness at end 60b at point of attachment 62 between breakaway tab 60 and cover member 14 than at end 60a at point of attachment 64 between breakaway tab 60 and cap member 50. In this configuration, when cap member 50 is disengaged from cover member 14, breakaway tab 60 severs at point of attachment 62 and remains integrally connected to cap member 50.

It therefore can be seen that breakaway tab 60 provides a temporary mechanism by which cap members 30, 40 and 50 are attached to cover member 14 of receptacle 12 prior to the engagement of cap members 30, 40 and 50 with pour spout port 16, vacuum port 18 and patient port 20. This temporary attachment of cap members 30, 40 and 50 prevents cap members 30, 40 and 50 from interfering with the connection of cover member 14 to receptacle 12 as cap members 30, 40 and 50 are maintained clear of the interior of receptacle 12 during the assembly process.

Whereas the present invention has been described with respect to specific embodiments thereof, it will be understood that various changes and modifications will be suggested to one skilled in the art and it is intended to encompass such changes and modifications as fall within the scope of the appended claims.

I claim:

1. In a suction system for draining fluid from a source, a receptacle cover comprising:
   (a) a plurality of ports located in the receptacle cover, including a first port for connection to a vacuum source, a second port for receiving fluid from the source and a third port for emptying collected fluid contained within the receptacle, said third port having a larger dimension than said first and second ports;
   (b) A first port closure member dimensioned to engage and close said first port, a second port closure member dimensioned to engage and close said second port and a third port closure member dimensioned to engage and close said third port, said third port closure member being larger than said first and second closure members;
   (c) a first flexible connecting line integrally molded and attached at one end to said first port closure member and at a second end to the receptacle cover at a first point of attachment for permanently attaching said first port closure member to the edge of the receptacle cover, said flexible connecting line having sufficient length to allow said first port closure member to engage and close said first port, a second flexible connecting line integrally molded and attached at one end to said second port closure member and at a second end to the receptacle cover at a second point of attachment for permanently attaching said second port closure member to the edge of the receptacle cover, and a third flexible connecting line integrally molded and attached at one end to said third port closure member and at a second end to the receptacle cover at a third point of attachment for permanently attaching said third port closure member to the edge of the receptacle cover; and
   (d) a separate breakaway tab means integrally molded and attached to each of said port closure members and to said receptacle cover for temporarily separately attaching each of said port closure members to the edge of the receptacle cover at a different point of attachment for each port closure member, said separate breakaway tab means spaced apart and distinct from said first, second and third points of attachment, each of said breakaway tab means being separable for allowing said port closure members to be disengaged from the receptacle cover at said points of attachment by said tab means to permit said port closure members to be moved to engage and close said ports, and each of said tab means having a portion of reduced thickness disposed adjacent said port closure members to provide a point of severance adjacent said port closure members.

* * * * *